(12) United States Patent
Park

(10) Patent No.: US 10,894,947 B1
(45) Date of Patent: Jan. 19, 2021

(54) METHOD FOR GENERATING PROTEIN RICH CONDITIONED MEDIUM

(71) Applicant: HOPE BIOSCIENCES, LLC, Sugar Land, TX (US)

(72) Inventor: Hyeonggeun Park, Sugar Land, TX (US)

(73) Assignee: HOPE BIOSCIENCES, LLC, Sugar Land, TX (US)

( * ) Notice: Subject to any disclaimer, the term of this patent is extended or adjusted under 35 U.S.C. 154(b) by 0 days.

(21) Appl. No.: 15/460,111

(22) Filed: Mar. 15, 2017

Related U.S. Application Data

(63) Continuation-in-part of application No. 15/142,135, filed on Apr. 29, 2016.

(51) Int. Cl.
 *C12N 5/0775* (2010.01)

(52) U.S. Cl.
 CPC ........ *C12N 5/0667* (2013.01); *C12N 2500/14* (2013.01); *C12N 2500/25* (2013.01); *C12N 2500/32* (2013.01); *C12N 2501/105* (2013.01); *C12N 2501/11* (2013.01); *C12N 2501/115* (2013.01); *C12N 2501/117* (2013.01); *C12N 2501/12* (2013.01); *C12N 2501/165* (2013.01); *C12N 2501/30* (2013.01)

(58) Field of Classification Search
 CPC .............. C12N 5/0667; C12N 2500/14; C12N 2500/25; C12N 2500/32; C12N 2501/105; C12N 2501/11; C12N 2501/115; C12N 2501/117; C12N 2501/12; C12N 2501/165; C12N 2501/30
 USPC ........................................................ 435/326
 See application file for complete search history.

(56) References Cited

U.S. PATENT DOCUMENTS

| 7,807,461 | B2 | 10/2010 | Kang et al. |
| 2007/0128685 | A1 | 6/2007 | Faudoa et al. |
| 2013/0089928 | A1 | 4/2013 | An et al. |
| 2015/0064273 | A1* | 3/2015 | Peled .................... A61K 35/28 424/574 |

FOREIGN PATENT DOCUMENTS

| WO | 2007123363 A1 | 11/2007 |
| WO | 2013032052 A1 | 3/2013 |

OTHER PUBLICATIONS

By Thermo Fisher Scientific, DMEM, high glucose, Available online at: www.thermofisher.com/us/en/home/technical-resources/media-formulation.8.html, Accessed Aug. 31, 2018.*
Minnesota Rural Water Association, Membrane Filtration, Available online at: www.mrwa.com/WaterWorksMnl/Chapter%2019%20Membrane%20Filtration.pdf, Accessed Sep. 1, 2018.*
Wager, et al. Replicative Senescence of Mesenchymal Stem Cells: A Continuous and Organized Process, PLoS One. 3(5):e2213 (2008).

* cited by examiner

*Primary Examiner* — Jennifer M. H. Tichy
(74) *Attorney, Agent, or Firm* — Rao Deboer Osterrieder, PLLC; Dileep P. Rao

(57) ABSTRACT

A method of creating a protein rich conditioned medium. The method includes culturing mesenchymal stem cells in a container utilizing a first growth medium, allowing a time period for proliferation of the mesenchymal stem cells until a desired level of confluence is achieved in the container, discarding a supernatant from the container, adding a second medium to the container, incubating the mesenchymal stem cells, and collecting the conditioned medium. The method produces significantly higher quantities of byproducts secreted by the mesenchymal stem cells. Byproducts are usable for wound healing, disease treatment, cosmetic, or other beneficial effects when applied or otherwise delivered to a patient.

9 Claims, 3 Drawing Sheets

FIG. 1

| REAGENTS | COMPONENT RANGES | A SAMPLE EMBODIMENT |
|---|---|---|
| KERATINOCYTE-BASED CELL GROWTH MEDIA (SERUM FREE MEDIUM) | BALANCE TO 100% VOL | BALANCE TO 100% VOL |
| FBS (FETAL BOVINE SERUM) | 0.1 ~ 50% VOL | ~ 10% VOL |
| ACIDIC-FGF (FIBROBLAST GROWTH FACTOR) OR BASIC-FGF (FIBROBLAST GROWTH FACTOR) | 1 pg/mL ~ 100 ng/mL | 1 ~ 10 ng/mL |
| EGF (EPIDERMAL GROWTH FACTOR) | 1 pg/mL ~ 100 ng/mL | 1 ~ 10 ng/mL |
| HYDROCORTISONE | 1 pg/mL ~ 100 μg/mL | 10 ~ 100 ng/mL |
| CALCIUM CHLORIDE | 1 nM ~ 100 mM | 0.01 ~ 0.1 mM |
| INSULIN | 1 ng/mL ~ 100 mg/mL | 0.5 ~ 5 mg/mL |
| BPE (BOVINE PITUITARY EXTRACT) | 1 pg/mL ~ 100 mg/mL | 10 ~ 100 μg/mL |
| L-CYSTEINE OR GLUTATHIONE | 1 nM ~ 100 mM | 0.5 ~ 5 mM |
| SELENIUM | 1 pg/mL ~ 100 mg/mL | 0.1 ~ 1 μg/mL |
| SDF-1 (STROMAL CELL-DERIVED FACTOR) | 1 pg/mL ~ 100 ng/mL | 1 ~ 10 ng/mL |
| SODIUM PYRUVATE | 1 ng/mL ~ 100 mg/mL | 2 ~ 20 mg/mL |
| TRANSFERRIN | 1 ng/mL ~ 100 mg/mL | 0.1 ~ 1 mg/mL |

FIG. 2

| | b-FGF | TGF-β1 | EGF | SDF-1α |
|---|---|---|---|---|
| METHODS KNOWN IN THE ART | 0.1 | 2 | 2 | 111 |
| PRESENT INVENTION | 2.5 | 24 | 42 | 520 |

FIG. 3

| | KGF(FGF-7) | IGF-1 | VEGF | HGF | PROCOLLAGEN | FIBRONECTIN |
|---|---|---|---|---|---|---|
| METHODS KNOWN IN THE ART | 0.240 | 0.48 | 3.490 | 3.377 | 28.597 | 164 |
| PRESENT INVENTION | 5.651 | 6.87 | 8.539 | 22.062 | 41.489 | 187 |

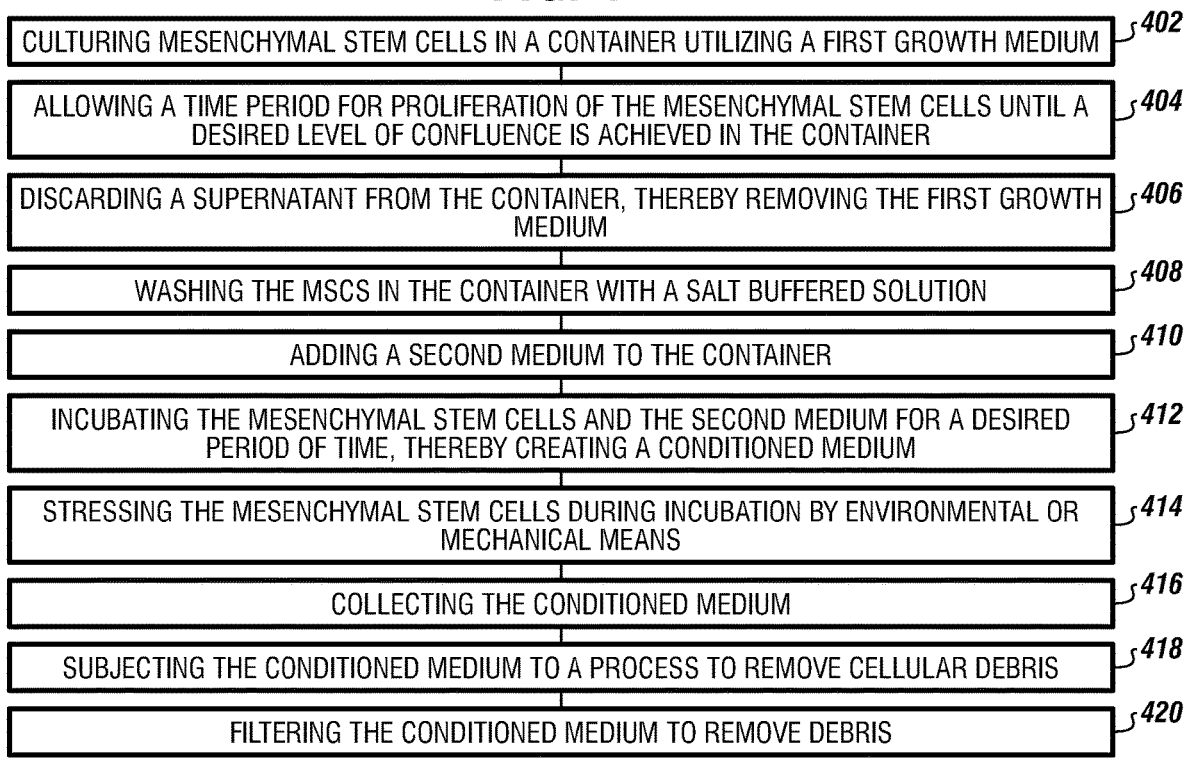

METHOD FOR GENERATING PROTEIN RICH CONDITIONED MEDIUM

CROSS REFERENCE TO RELATED APPLICATION

The current application is a Continuation in Part and claims priority to co-pending Application Ser. No. 15/142,135 filed on Apr. 29, 2016, entitled "CULTURE MEDIA FOR MULTIPOTENT STEM CELLS". This reference is hereby incorporated in its entirety.

FIELD

The present embodiments generally relate to a method of creating a protein rich conditioned medium from media used for culturing mesenchymal stem cells (MSCs).

BACKGROUND

Stem cells are cells that have the potential to develop into different cell types in the body during early life and growth. They have the ability to self-renew and are integral in the body's natural repair process. There are two primary sources of stem cells, embryonic and non-embryonic or adult stem cells. Adult stem cells are found in practically every tissue or organ in the body. They too have the ability to self-renew and differentiate into a multitude of specialized cell types.

Mesenchymal stem cells (MSCs) are a specific group of mesoderm origin adult stem cells that are pluripotent. Being pluripotent, they have multi-directional differentiation capabilities. They can become fat, bone, cartilage, tendons, muscle, nerves, ligaments, liver, cardiac muscle, endothelial cells, pancreatic islet cells and many others. In addition, they are cells with low immunogenicity and are naturally immune-modulatory cells. Given their versatility, MSCs have quickly become an ideal cell type used in therapeutics for degenerative and autoimmune conditions, amongst other ailments.

MSCs have the unique ability to navigate or "home" to areas of injury and/or degeneration. When the body is in need of repair it sends out signals to mobilize stem cells to begin the repair process. MSCs not only differentiate but increase angiogenesis and excrete anti-inflammatory cytokines and growth factors. MSCs were originally found in bone marrow. It was soon discovered that in elderly or ill adults, the MSC content in bone marrow is extremely low. Low stem cell yield and a painful donation process led scientists to look for other, more easily available sources of MSCs in the body.

While the present invention deals with MSCs from any source, the current state of the art suggests that MSCs derived from adipose tissue (body fat) are the easiest and most practical to harvest and culture for various uses. However, the present disclosure is intended to encompass MSCs derived from any source, such as bone marrow, umbilical cord tissue, molar cells, amniotic fluid, or any other source known to persons having ordinary skill in the art.

Adipose tissue contains approximately 100,000 MSCs per gram of fat. It is a naturally rich source of MSCs, and the MSCs harvested therefrom are mostly unaffected by age or the donor's condition. Fat is becoming very popular as a stem cell source because of stem cell quality, properties, ease of extraction, and in most cases, ample availability.

Having a large amount of fat tissue may translate into a high stem cell count but acquiring a large amount is a fairly invasive procedure. Liposuction often requires general anesthesia and vacuum suction. When machine suction is used, cells are often broken and injured during the extraction process. Therefore, small, localized syringe extractions are ideal. In a typical case, a 5 gram extraction of fat would yield approximately 500,000 MSCs. To reach therapeutic quantities of MSCs (in the millions or billions), in vitro cell culture is a suitable solution.

Culturing fat derived MSCs is currently much easier as compared to other MSCs. Adipose derived MSCs generally proliferate well and behave consistently regardless of the donor's age or condition.

However, when utilizing currently existing culturing methods, the MSC proliferative potential and characteristics are continuously decreased during prolonged culture. For example, it has been shown that expansion in culture leads to premature senescence (the process of aging characterized by continuous morphological and functional changes). Cells became much larger with irregular and flat shape and the cytoplasm became more granular.

These senescence-associated effects are continuously acquired from the onset of in vitro culture. As a result, the successful manufacturing for commercialization of large batches from one donor of homogenous MSCs that preserve their characteristics following expansion in culture remains a challenge.

Methods for increasing proliferation and survival in MSCs have been widely studied over the past few years and many factors have been proposed for increasing the expansion efficiency of these cells.

For example, many protocols relating to the expansion of MSCs include culturing in the presence of basic fibroblast growth factor (b-FGF). It has been shown that b-FGF not only maintains MSC proliferation potential, it also retains osteogenic, adipogenic and chondrogenic differentiation potentials through the early mitogenic cycles. Vascular endothelial growth factor (VEGF) has also been shown to increase MSC proliferation. Hepatocyte growth factor (HGF) has been shown to affect proliferation, migration and differentiation. Platelet derived growth factor (PDGF) shown to be a potent mitogen of MSCs. Epidermal growth factor (EGF) and heparin-binding EGF have both been shown to promote ex vivo expansion of MSCs without triggering differentiation into any specific lineage. In addition to its mitogenic effect on MSCs, EGF also increases the number of colony-forming units by 25 percent.

The present invention makes use of a new growth medium which allows for MSC proliferation without the MSC characteristics being continuously decreased during prolonged culture. As such, a greater quantity of stable MSCs can be achieved in culture.

When culturing MSCs in a growth medium, protein byproducts and non-protein byproducts are secreted by the MSCs as they proliferate and continue to be secreted when MSCs have been cultured. The protein byproducts can have significant wound healing, disease treatment, cosmetic, or other beneficial effects when applied or otherwise delivered to a patient. A medium containing such byproducts can be referred to as a conditioned medium.

The protein byproducts have the benefit of being the pure active ingredient desirable for medical treatments or cosmetic applications. Further, the protein byproducts are sterile and safe to use in virtually any circumstance.

While usage of a conditioned medium and creation thereof is known in the art, the present invention allows for significantly higher quantities of various desirable proteins in the conditioned medium. Previous methods have been limited by the ability to culture stem cells rapidly and without degradation to allow for greater quantities of stem cells to secrete desirable protein byproducts.

The present invention allows for rapid and efficient culture of MSCs, thereby greatly increasing the quantity of byproduct secretion. The conditioned medium derived therefrom contains significantly greater levels of desired proteins and, potentially, other non-protein byproducts.

A need exists for a method of cell culture which allows for rapid MSC proliferation without any degradation of the MSC characteristics. Further, a need exists for a method to maximize generation of beneficial byproducts for medical, cosmetic, or other uses. While protein byproducts are the focus of this disclosure, there may be other useful and beneficial non-protein MSC secretions in the conditioned medium, and these secretions can be harvested in the same manner as described below.

The present invention meets the above needs.

BRIEF DESCRIPTION OF THE DRAWINGS

The detailed description will be better understood in conjunction with the accompanying drawings as follows:

FIG. 1 is an example embodiment of the first growth medium.

FIG. 2 is a comparison of the quantity of specific proteins generated by the present invention to methods known in the art.

FIG. 3 is a comparison of the quantity of specific proteins generated by the present invention to methods known in the art.

FIG. 4 is a chart illustrating the steps of one embodiment of the present invention.

The present embodiments are detailed below with reference to the listed Figures.

DETAILED DESCRIPTION OF THE EMBODIMENTS

Before explaining the present invention in detail, it is to be understood that the invention is not limited to the specifics of particular embodiments as described and that it can be practiced, constructed, or carried out in various ways.

While embodiments of the disclosure have been shown and described, modifications thereof can be made by one skilled in the art without departing from the spirit and teachings of the disclosure. The embodiments described herein are exemplary only, and are not intended to be limiting.

Specific structural and functional details disclosed herein are not to be interpreted as limiting, but merely as a basis of the claims and as a representative basis for teaching persons having ordinary skill in the art to variously employ the present invention. Many variations and modifications of embodiments disclosed herein are possible and are within the scope of the present disclosure.

Where numerical ranges or limitations are expressly stated, such express ranges or limitations should be understood to include iterative ranges or limitations of like magnitude falling within the expressly stated ranges or limitations.

The use of the word "a" or "an" when used in conjunction with the term "comprising" in the claims and/or the specification may mean "one," but it is also consistent with the meaning of "one or more," "at least one," and "one or more than one."

The word "about" means plus or minus 5 percent of the stated number.

The use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description herein, but is only limited by the claims which follow, encompassing all equivalents of the subject matter of the claims. Each and every claim is incorporated into the specification as an embodiment of the present disclosure. Thus, the claims are a further description and are an addition to the preferred embodiments of the present disclosure.

The inclusion or discussion of a reference is not an admission that it is prior art to the present disclosure, especially any reference that may have a publication date after the priority date of this application. The disclosures of all patents, patent applications, and publications cited herein are hereby incorporated by reference, to the extent they provide background knowledge; or exemplary, procedural or other details supplementary to those set forth herein.

The present embodiments generally relate to a method of creating a protein rich conditioned medium from media used for culturing mesenchymal stem cells (MSCs). While human stem cells are the subject of the present disclosure, it is contemplated that all mammalian stem cells would respond to the culture as disclosed. In the spirit of enablement and clarity, human stem cells are utilized to describe the invention below.

Exemplary proteins secreted by MSCs include, but are not limited to: Keratinocyte growth factor (KGF)(for example growth factor FGF7), Insulin-like growth factors (IGFs), Vascular endothelial growth factor (VEGF)(originally known as vascular permeability factor (VPF)), Epidermal growth factor (EGF), Hepatocyte growth factor (HGF) (or scatter factor (SF)), Stromal cell derived factor (SDF), Transforming growth factor (TGF), Collagen and pre-collagen components such as procollagen, and Fibronectin.

Serum, as used within this disclosure, refers to the remaining fraction after removal of coagulation and red blood cells from any mammalian blood. Exemplary serums used for cell culture as known to persons having ordinary skill in the art include, but are not limited to: fetal bovine serum (also known as fetal calf serum), horse serum, mouse serum, goat serum, rabbit serum, rat serum, human serum, and the like. Serum is also intended to encompass synthetic or recombinant equivalents, or other equivalents as known to persons having ordinary skill in the art, such as Human Platelet Lysate (hPL).

Fibroblast growth factors and epidermal growth factors, as used within this disclosure, refers to families of proteins, hormones, or other naturally occurring substances that promote cell growth, proliferation, and/or differentiation. Members are typically involved in angiogenesis, wound healing, embryonic development, and various endocrine signaling pathways. Synthetic, recombinant, or other equivalents are also covered within the scope of this disclosure.

Pituitary extract, as used within this disclosure, refers to hormones extracted from the pituitary gland, such as oxytocin or vasopressin. Any mammalian pituitary extracts and their equivalents can be utilized. Synthetic, recombinant, or other equivalents are also covered within the scope of this disclosure.

L-Cysteine, as used within this disclosure, refers to the amino acid as known to persons having ordinary skill in the art. Synthetic, recombinant, or other equivalents are also covered within the scope of this disclosure.

Glutathione, as used within this disclosure, refers to an antioxidant found in plants, animals, fungi, bacteria, or other living organisms. Synthetic, recombinant, or other equivalents are also covered within the scope of this disclosure.

N-Acetyl Cysteine (NAC), as used within this disclosure, refers to a protein that potentially participates in self-renewal and pluripotency in stem cells. Synthetic, recombinant, or other equivalents are also covered within the scope of this disclosure.

Selenium, as used within this disclosure, refers to the non-metal chemical element with the symbol Se. Synthetic, recombinant, or other equivalents are also covered within the scope of this disclosure.

Stromal-derived factor, as used within this disclosure, refers to proteins belonging to the chemokine family which promote growth, survival, and development of stem cells. Synthetic, recombinant, or other equivalents are also covered within the scope of this disclosure.

Sodium pyruvate, as used within this disclosure, refers to a compound commonly added to cell culture media to provide an additional source of energy. Synthetic, recombinant, or other equivalents are also covered within the scope of this disclosure.

Transferrin, as used within this disclosure, refers to iron binding proteins commonly found in blood. Any mammalian transferrin and equivalents can be utilized. Synthetic, recombinant, or other equivalents are also covered within the scope of this disclosure.

Serum-free medium, as used within this disclosure, refers to a basal medium. A basal medium can be any medium designed to support the growth of microorganisms or cells.

The method of creating a protein rich conditioned medium can have the following steps:

Culturing mesenchymal stem cells in a container utilizing a first growth medium. Any container known to persons having ordinary skill in the art can be utilized. The first growth medium can comprise a serum, a fibroblast growth factor, and either an L-cysteine, a glutathione, or a N Acetyl Cysteine (NAC). While the disclosure emphasizes the use of adipose derived stem cells, any MSC can be utilized for culture.

Optionally, the first growth medium can also contain various quantities of an epidermal growth factor, a hydrocortisone, a calcium chloride, an insulin, a pituitary extract, a selenium, a stromal-derived factor, a sodium pyruvate, a transferrin, and serum-free medium.

Allowing a time period for proliferation of the mesenchymal stem cells until a desired level of confluence is achieved in the container. Confluence in this disclosure refers to the proportion or percentage of the container surface covered by MSCs.

Discarding a supernatant from the container, thereby removing the first growth medium.

Optionally, washing the MSCs in the container with a salt buffered solution.

Adding a second medium to the container. The second medium can be a serum-free medium, or a salt buffered solution. In embodiments, the salt used can be a calcium salt or a magnesium salt.

The second medium typically does not contain components encouraging the MSCs to proliferate. This allows for all of the MSC resources to be devoted to secreting protein or non-protein byproducts instead of reproducing, thereby maximizing the quantity of byproducts.

Incubating the mesenchymal stem cells and the second medium for a desired period of time, thereby creating a conditioned medium. Persons having ordinary skill in the art can adjust incubation times and temperatures for optimal results. A typical set of parameters can be at a temperature from about 35 degrees Celsius to about 40 degrees Celsius for a period of about 1 day to about 7 days.

While typically, the vast majority of the results are achieved within 2 days of incubation, longer periods can be implemented as necessary without detriment to either the MSCs or the protein byproducts. Time frames of up to 30 days have been tested, at which point MSCs start to die within the culture.

Further, as known in the art, stressing the MSCs, such as by removing the food source can accelerate protein byproduct production. During incubation, subjecting the MSCs to environmental or mechanical stresses may further enhance byproduct secretion by the MSCs. Exemplary stresses include, but are not limited to: starving the MSCs, manipulating the temperature, manipulating the atmosphere, vibrating the container, spinning the container, or other methods known to persons having ordinary skill in the art.

Collecting the conditioned medium by decanting the supernatant.

Optionally, the conditioned medium can be subjected to a process to remove cellular debris, such as centrifuging the conditioned medium for a duration at a desired speed. Persons having ordinary skill in the art can select from any known methods and parameters for removing cellular debris.

Optionally, filtering the conditioned medium to remove debris. In embodiments, the filter can have a pore size ranging from 0.1 µm to 0.45 µm.

The conditioned medium contains various protein byproducts produced by the MSCs. Exemplary proteins include, but are not limited to: Keratinocyte growth factor (KGF)(for example growth factor FGF7), Insulin-like growth factors (IGFs), Vascular endothelial growth factor (VEGF)(originally known as vascular permeability factor (VPF)), Epidermal growth factor (EGF), Hepatocyte growth factor (HGF) (or scatter factor (SF)), Stromal cell derived factor (SDF), Transforming growth factor (TGF), Collagen and pre-collagen components, and Fibronectin.

While protein byproducts are discussed within the present disclosure, other beneficial non-protein byproducts may be secreted by the MSCs.

The present invention leads to much greater yields of the protein byproducts than by utilizing methods currently known in the art. The growth medium as disclosed allows for MSCs to proliferate without degrading, thereby continuing to produce protein byproducts recovered in the conditioned medium.

EXAMPLE EMBODIMENT

Human adipose tissue-derived mesenchymal stem cells were cultured with a first growth medium containing fetal bovine serum, a fibroblast growth factor, and either L-Cysteine, Glutathione, or NAC in a normal cell culture environment. Temperature was maintained at 37 degrees Celsius, with a carbon dioxide concentration of 5 percent.

Upon reaching a confluence of at least 90 percent, the supernatant was discarded and the cultured MSCs were washed with a salt buffered solution. The salt buffered solution contained Calcium and Magnesium salts.

After washing the MSCs, a second medium (serum free medium was added to the cultured MSCs.

The MSCs were incubated for approximately 2 days in normal cell culture environment to allow for the secretion of protein byproducts into the second medium.

The second medium was then collected as the conditioned medium.

In this instance, the conditioned medium was centrifuged for 10 minutes at 2000 revolutions per minute in order to remove cellular debris.

In this instance, the conditioned medium was further filtered for purification, thereby creating the final conditioned medium.

Turning now to the Figures, FIG. 1 is an example embodiment of the first growth medium. Listed are general component ranges for various components usable as the first growth medium, as well as a sample embodiment. It should be understood that the range limits can vary by 5 percent of the stated value.

FIG. 2 is a comparison of the quantity of specific proteins generated by the present invention to methods known in the art. The chart displays relative quantities of various proteins in pg/ml in conditioned media as created by methods known in the art in comparison to quantities of various proteins in conditioned media as created by the present invention.

FIG. 3 is a comparison of the quantity of specific proteins generated by the present invention to methods known in the art. The chart displays relative quantities of various proteins in ng/ml in conditioned media as created by methods known in the art in comparison to quantities of various proteins in conditioned media as created by the present invention.

FIG. 4 is a chart illustrating the steps of one embodiment of the present invention.

The method can comprise step 402, culturing mesenchymal stem cells in a container utilizing a first growth medium. The first growth medium can comprise a serum, a fibroblast growth factor, and either an L-cysteine, a glutathione, or a N Acetyl Cysteine (NAC). Optionally, the first growth medium can also contain various quantities of an epidermal growth factor, a hydrocortisone, a calcium chloride, an insulin, a pituitary extract, a selenium, a stromal-derived factor, a sodium pyruvate, a transferrin, and serum-free medium.

The method can comprise step 404, allowing a time period for proliferation of the mesenchymal stem cells until a desired level of confluence is achieved in the container.

The method can comprise step 406, discarding a supernatant from the container, thereby removing the first growth medium.

The method can comprise step 408, washing the MSCs in the container with a salt buffered solution.

The method can comprise step 410, adding a second medium to the container. The second medium can be a serum-free medium, or a salt buffered solution.

The method can comprise step 412, incubating the mesenchymal stem cells and the second medium for a desired period of time, thereby creating a conditioned medium.

The method can comprise step 414, stressing the mesenchymal stem cells during incubation by environmental or mechanical means.

The method can comprise step 416, collecting the conditioned medium.

The method can comprise step 418, subjecting the conditioned medium to a process to remove cellular debris, such as centrifuging the conditioned medium for a specific duration at a desired speed.

The method can comprise step 420, filtering the conditioned medium to remove debris. In embodiments, the filter can have a pore size ranging from 0.1 μm to 0.45 μm.

While the invention has been described with emphasis on the presented embodiments and Figures, it should be understood that within the scope of the appended claims, the invention might be practiced other than as specifically enabled herein.

What is claimed is:

1. A method of creating a protein rich conditioned medium comprising:
   a) culturing mesenchymal stem cells in a container utilizing a first growth medium,
      wherein the first growth medium comprises:
      i) a serum from about 1 percent to about 10 percent by volume;
      ii) fibroblast growth factor from about 1 ng/ml to about 10 ng/ml;
      iii) an L-cysteine or a glutathione or an N Acetyl Cysteine from about 0.5 mM to about 5 mM; and
      iv) a serum free medium up to 99 percent volume and:
         1) an epidermal growth factor from about 1 ng/ml to about 10 ng/ml;
         2) a hydrocortisone from about 10 ng/ml to about 100 ng/ml;
         3) a calcium chloride from about 0.01 mM to about 0.1 mM;
         4) an insulin from about 0.5 mg/ml to about 5 mg/ml;
         5) a bovine pituitary extract from about 10 μg/ml to about 100 μg/ml;
         6) a selenium from about 0.1 μg/ml to about 1 μg/ml;
         7) a stromal-derived factor from about 1 ng/ml to about 10 ng/ml;
         8) a sodium pyruvate from about 2 mg/ml to about 20 mg/ml; and
         9) a transferrin from about from about 0.1 mg/ml to about 1 mg/ml;
   b) allowing a time period for proliferation of the mesenchymal stem cells until a desired level of confluence is achieved in the container;
   c) discarding a supernatant from the container;
   d) adding a second serum-free medium or a salt buffered solution to the container;
   e) incubating the mesenchymal stem cells and the second serum-free medium or the salt buffered solution for a desired period of time, thereby creating a conditioned medium; and
   f) collecting the conditioned medium; and
   wherein the mesenchymal stem cells can be incubated for up to seven days in the second medium without change in mesenchymal stem cell characteristics.

2. The method of claim 1, wherein at least a 90 percent confluence is achieved.

3. The method of claim 1, further comprising the step of washing the mesenchymal stem cells after discarding the supernatant and prior to adding the second medium.

4. The method of claim 3, wherein the mesenchymal stem cells are washed with a salt buffered solution.

5. The method of claim 4, wherein the salt is a calcium salt or a magnesium salt.

6. The method of claim 1, wherein collected conditioned medium is subjected to a process to remove cellular debris.

7. The method of claim 6, wherein the process is centrifuging the conditioned medium.

8. The method of claim 1, wherein collected conditioned medium is passed through a filter.

9. The method of claim 8, wherein the filter has a pore size ranging from about 0.1 μm to about 0.45 μm.

\* \* \* \* \*